United States Patent
Uchitel et al.

(10) Patent No.: US 9,845,284 B1
(45) Date of Patent: Dec. 19, 2017

(54) METHOD OF OBTAINING COMPLEX ACIDIC SALTS OF DIVALENT METALS AND DICARBOXYLIC ACIDS

(71) Applicants: Mikhail Lvovich Uchitel, Mytishi (RU); Roman Anatolievich Trunin, Moscow (RU); Evgenij Iljich Maevskij, Pushino (RU)

(72) Inventors: Mikhail Lvovich Uchitel, Mytishi (RU); Roman Anatolievich Trunin, Moscow (RU); Evgenij Iljich Maevskij, Pushino (RU)

( * ) Notice: Subject to any disclaimer, the term of this patent is extended or adjusted under 35 U.S.C. 154(b) by 0 days.

(21) Appl. No.: 15/368,618

(22) Filed: Dec. 4, 2016

(30) Foreign Application Priority Data

Sep. 16, 2016 (RU) .................. 2016137257

(51) Int. Cl.
*C07C 229/00* (2006.01)
*C07C 227/18* (2006.01)
*C07C 51/41* (2006.01)

(52) U.S. Cl.
CPC .......... *C07C 227/18* (2013.01); *C07C 51/418* (2013.01)

(58) Field of Classification Search
CPC .............................. C07C 27/18; C07C 51/418
See application file for complete search history.

(56) References Cited

PUBLICATIONS

Shao-yu et al. (Studies on Synthesizing Magnesium Aspartate as a Feed Journal of Henan Agricultural Sciences, (6), pp. 87-89, Published 2005.*
Shao-yu et al. (Studies on Synthesizing Magnesium Aspartate as a Feed Journal of Henan Agricultural Sciences, (6), pp. 87-89, Published 2005 translated.*

* cited by examiner

*Primary Examiner* — Yevgeny Valenrod
*Assistant Examiner* — Blaine G Doletski
(74) *Attorney, Agent, or Firm* — Bardmesser Law Group

(57) ABSTRACT

A method of obtaining a complex acidic salt of a divalent metal and a dicarboxylic acid includes heating water in a reactor; adding a dicarboxylic acid to the heated water; stirring the water to dissolve the dicarboxylic acid in the heated water to produce a solution or a suspension of the dicarboxylic acid in the heated water; adding MeO to the solution or the suspension, where Me is a divalent metal; continuing the stirring of the solution or suspension until formation of the complex acidic salt $Me(AcH)_2 \cdot nH_2O$ begins, where Ac is an anion of the dicarboxylic acid, and n=0-8; cooling the complex acidic salt to below a temperature of crystallization; sedimenting the complex acidic salt; filtering the complex acidic salt to remove water from the complex acidic salt; and drying the complex acidic salt.

3 Claims, No Drawings

METHOD OF OBTAINING COMPLEX ACIDIC SALTS OF DIVALENT METALS AND DICARBOXYLIC ACIDS

CROSS-REFERENCE TO RELATED APPLICATIONS

This application claims priority to RU 2016137257, filed on Sep. 16, 2016, which is incorporated by reference herein in its entirety.

BACKGROUND OF THE INVENTION

Field of the Invention

The invention relates to the area of chemical production, and, particularly, to the area of industrial salt production, namely complex salts of divalent metals and dicarboxylic acids.

Description of the Related Art

Complex salts of divalent metals and dicarboxylic acids with a general formula $Me(AcH)_2 \cdot nH_2O$, (I), where Me—a divalent cation, Ac—an anion of a dicarboxylic acid, H—hydrogen, $n \geq 0$, are used in medicine, cosmetology, veterinary medicine, and food production and processing. In medicine, including veterinary, such compounds are used to provide an effective transmembrane delivery of divalent metal cations [1], which are necessary to prevent and treat a wide spectrum of conditions.

Currently, a large number of methods for preparing such salts are known; however, all of these methods have characteristics of laboratory techniques. Obtaining such complex salts of high purity is difficult and expensive, because usually an entire spectrum of compounds is formed during synthesis—from neutral salts (biologically ineffective) to complex salts with variable composition. The biological effects of the latter are not studied, and they are not allowed to be used in food, pharmaceutical and veterinary industries.

In addition, the production of such salts is made more difficult by the drying process. Most of the known technical solutions do not produce salts with structures that allow conversion to an anhydrous state after drying. This may be because, during synthesis, one of the water molecules becomes "coordinated" in the salt structure and subsequently determines degree of hydration.

Complex compounds of divalent cations (Cd, Ca, Mg, Ni, Zn, Cu, Fe and others) with amber, aspartic and fumaric acids are synthesized via reactions with the corresponding acids (in melted, aqueous solution or suspension forms) or its sodium (potassium) salts with salts (carbonates, chlorides, nitrates etc.), oxides, hydroxides, and complex compounds (including aquachelates) of the corresponding cations [2-6].

One of the known solutions [7] proposes to obtain salts of amber acid by hydrogenation of the corresponding salts of maleic and fumaric acids; however, this method does not produce salts of unsaturated acids and does not allow synthesis of complex acidic salts. The products of such synthesis are neutral salts with AcMe structure, where Ac is amber acid anion, Me is divalent metal.

Known synthesis methods of salts of dicarboxylic acid [8,9] are fairly exotic and are conducted under stringent conditions: heating a mixture of alcohol (for example, butanol), metal hydroxide, and water under 50-500 atm, to 250-400° C. [8] or a carbon monoxide treatment of acetate and metal carbonate mixture at 300-450° C. [9].

The types of synthesis described above produce mixtures of complex compounds that differ not only in the M to L ratios, but also in their structures. This fact was proven by the studies we have conducted: depending on the conditions of the synthesis and chemical properties of cations and anions, the Ac:Me ratio range varies widely (1:1, 1:2, 1:3, 1:4, 1:5, 2:1, 2:3). Stability constants of complexes with different Ac:Me ratios and their solubility in water sometimes differ significantly; this makes it more difficult to obtain, in an aqueous environment, compounds of homogenous composition. For example, water solubility of divalent cation succinates (neutral salts MeSuc) is significantly lower than that of complex compounds with the ratio Me:Suc<1. In addition, for example, for complexes $CaSuc_n$ (where 2<n<5) water solubility depends on n and reaches a maximum when n~3. An inverse relationship exists for fumarates: solubility of MeFum is higher than that of complexes with the ratio Me:Fum<1.

If, in order to get complex salts with the structure $Me(AcH)_2$, initial components ("basic" and "acidic") are added in the 1:2 ratio to an aqueous environment (as done, for example in [7]), then, in addition to $Me(AcH)_2$, the products of the reaction will also contain compounds such as MeAc and $Me(AcH)_3$; for example, this will be in the case in the following reactions:

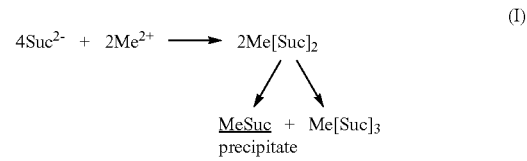

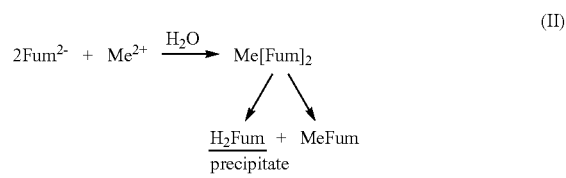

As a result of reaction (I), during crystallization of the target compound $Me[Suc]_2$, there is co-precipitation of a poorly-soluble neutral salt MeSuc (that is for all practical purposes not metabolized by animals); the equivalent amount of a more soluble $Me[Suc]_3$, will mostly be in the solution. Recombination of fumarates $Me[Fum]_2$ in reaction (II) results in a precipitation that, in addition to the target compound, also contains some fumaric acid, while a partially equivalent amount of a more soluble MeFum will be in the solution (MeFum is more soluble than $H_2Fum$ and $Me[Fum]_2$). Reliable differentiation between the target and waste products in these reactions is either extremely time-consuming and expensive, or impossible.

Usually, when a compound with the ratio Me:Ac<1 is the target of a reaction, a "basic" component or its solution is added to the solution of an "acidic" component (if the order is reversed, then there is definitely a preferential formation of low solubility MeAc complexes, which have little interactions even with an excess of "acidic" components). However, even if synthesis is conducted using the "usual"

method, which is proposed in most of the above-mentioned cases, such as in [10], there are constant changes in concentrations and ratios of the reagents in the reaction zone. This also does not facilitate production of individual complexes with a defined ratio Me:Ac; the product of the reaction is a mixture of complexes and their ratios cannot be reliably replicated. This makes it impossible to use these methods for industrial production of the target products—complex salts of divalent metals and carboxylic acids.

In addition, it is known that in aqueous solutions, cations with variable charges always form aqua-complexes [Me$(H_2O)n$]2+ that have one or more water molecules (depending on the coordinating number of a given cation) acting as a ligand. These aqua-complexes form as a result of water molecules forming bonds or cation hydration—if a "basic" component was previously dissolved (suspended) in water. They can also form from other coordinated compounds as a result of inner-substitution when other methods of initial components introduction to the reaction are used.

That is why complex salts $Me_n Ac_m \cdot xH_2O$ contain not only crystallized water, connected with the anion, but also a stable coordinated water that is positioned in a specific way around the cation. The character of the bond is determined, among others, by the conditions of the synthesis (temperature, speed and the order in which components are added, crystallization conditions, incubation time, drying conditions, etc.).

In order to minimize impurities content in the target complex (impurities that appear as the result of hydrolysis, recombination, or inner-substitution), methods of synthesis in non-aqueous environments (for example, in absolute alcohols and chloroform) are proposed [5, 6, 11]. Such methods are acceptable as preparatory, however, with scaled production, the use of organic solvents complicates the technology (regeneration of the solvent), and lowers production volume (low solubility of initial components in organic solvents), thus making the target product more expensive. Moreover, the presence of remaining alcohols (except ethyl alcohol) and chloroform in the final product is not permitted based on the food safety requirements, and their complete elimination from the final product is quite difficult. All of this makes it impossible to use these known technologies for industrial production.

In RU patent 02115657 the authors propose synthesis and use of aquachelates that "include biogenic metal and at least one organic ligand . . . . A metal is selected from . . . metal groups "f", "d", "p", preferably Cs, Mg, Ca, In, Se, Te, Fe (II), Fe (III), Co (II), Co (III), Mn (II), Cu, Ni, Zn. A ligand is selected from amino acids . . . carboxylic acids . . . ".

A known method of obtaining "aquachelates" (RU 2115657) is essentially an interaction of aqueous solutions of a metal salt and a ligand, "amount of which is carefully checked in order to regulate stoichiometry between the ligand and the metal . . . ratio of the metal and the ligand are set at 1:0.5; 1:1; 1:1.5; 1:2 . . . after formation of 'aquachelates" part or all of the water can be removed from the solution . . . until the aquachelates takes the form of dry powder . . . the aquachelate can be dehydrated to remove all labile water, and the labile water is reconstituted".

The main limitation of the above-described method (RU 2115657) is that it is impossible to get individual complex composition with a predetermined ratio of a metal and a ligand (discussed in detailed above); the method allows only to get a mixture of complexes.

Japanese patent No. 49-8849, 1965 and its analogues [10] describes calcium succinate complexes $Ca(Suc)_n$, where $2<n<5$, are obtained as follows: calcium carbonate and amber acid in molar ratio 1-2 to 1-5 (depending on the ratio of Ca:Suc in the target complex) are dissolved in 5× amount of water (relative to amber acid), incubated for 24 hours at room temperature, and filtered. The resulting solution is slowly heated to 100° C. with stirring, and all of the water is slowly evaporated. Three hours after the start of evaporation, the crystals begin to form; after 6 hours the evaporation is complete.

Limitations of the method described above [10] are:

1. Length of the procedure: 24-hour incubation followed by a lengthy, slow evaporation. In order to receive 129 g of the product, <1 L of the reactive mass is evaporated for 6 hours; and the composition and quality of the precipitate is not discussed.

2. Non-homogenous composition of the precipitate formed during evaporation: the precipitate formed at the beginning of evaporation contains less soluble complexes (based on NMR and IR spectroscopy). For example, during synthesis of $Ca(Suc)_3$ complex, other less soluble complexes will first crystallize and then precipitate—CaSuc, $Ca(Suc)_2$, $Ca(Suc)_4$, $Ca(Suc)_5$; during synthesis of $Ca(Suc)_2$-CaSuc, $Ca(Suc)_4$ and $Ca(Suc)_5$ will also crystallize and precipitate.

3. During pre-filtration process, one of the reagents can be partially removed together with mechanical additives. Consequently, even a small change in the initial ratio of the reagents will result in a less homogeneous composition of the product (described in 2, above).

SUMMARY OF THE INVENTION

Accordingly, the present invention is related to a method of obtaining complex acidic salts of divalent metals and dicarboxylic acids that substantially obviates one or more of the disadvantages of the related art.

An exemplary method of obtaining a complex acidic salt of a divalent metal and a dicarboxylic acid includes heating water in a reactor; adding a dicarboxylic acid to the heated water; stirring the water to dissolve the dicarboxylic acid in the heated water to produce a solution or a suspension of the dicarboxylic acid in the heated water; adding MeO to the solution or the suspension, where Me is a divalent metal; continuing the stirring of the solution or suspension until formation of the complex acidic salt $Me(AcH)_2 \cdot nH_2O$ begins, where Ac is an anion of the dicarboxylic acid, and n=0-8; cooling the complex acidic salt to below a temperature of crystallization; sedimenting the complex acidic salt; filtering the complex acidic salt to remove water from the complex acidic salt; and drying the complex acidic salt.

Additional features and advantages of the invention will be set forth in the description that follows, and in part will be apparent from the description, or may be learned by practice of the invention. The advantages of the invention will be realized and attained by the structure particularly pointed out in the written description and claims hereof as well as the appended drawings.

It is to be understood that both the foregoing general description and the following detailed description are exemplary and explanatory and are intended to provide further explanation of the invention as claimed.

DETAILED DESCRIPTION OF THE PREFERRED EMBODIMENTS

Reference will now be made in detail to the preferred embodiments of the present invention.

The objective is a process that results in a more effective method of synthesis of complex salts with a general formula:

Me(AcH)$_2$.nH$_2$O, (I), where Me—divalent cation, Ac—anion of dicarboxylic acid, H—hydrogen, n≥0. There is a need for synthesis of complexes with defined composition, because complexes with the same composition but with different Me:Ac ratios have different physical, chemical, and biological properties, and complex salts that have the same composition but different degrees of hydration have different pharmacokinetics and different abilities to interact with other components of drugs and foods.

The presented problem is solved by conducting the synthesis in such a way that constant, equal to the initial, ratios between all components of the reaction are maintained in the reaction volume.

To do this, an oxide of divalent metal dissolved in water immediately before the reaction is used as a "basic" agent. The reaction is conducted with stirring, in a way that provides mixing of the entire volume in the reactor; control of the flow speed provides turbulent movement of the fluid.

In practice, to obtain a salt with the ratio Me:Ac=1:2, components are added to the reactor not with the stoichiometric ratio 1:2, but with molar ratio MeO:AcH$_2$=1:2.005-1:2.10. Decrease of the ratio below 2.01 leads to the formation of neutral salts; increase in the ratio above 2.10 leads to the formation of salts that will have more than 2 dicarboxylic acid anions in their structure.

Oxides of zinc, magnesium, and calcium are most often used as metal oxide reagents; amber, fumaric, L-aspartic, L,D-aspartic acids—as dicarboxylic acid reagents.

The proposed method allows producing complex acidic salts of divalent metals and dicarboxylic acids with given composition with the main product making up at least 95% of the mass. The product can be either completely dehydrated during drying or have a predetermined amount of water.

Salts obtained by the method proposed here do not have biological activities on their own; their combination makes them potentially very useful for activation and regulation of a number of main metabolic processes in animals. Based on the proposed invention, when combined with other compounds, the biological activity of complex salts becomes extremely high and not replaceable by other known substances with identified biological activity. There is a pronounced synergetic effect, which cannot be obtained by other means.

Key to the symbols provided in the examples below:
SucH$_2$ HOOC—CH$_2$—CH$_2$—COOH—amber acid
SucH HOOC—CH$_2$—CH$_2$—COO$^-$—amber acid anion
FumH$_2$ HOOC—CH=CH—COOH—fumaric acid
FumH HOOC—CH=CH—COO$^-$—fumaric acid anion
AspH$_2$ HOOC—CH(NH$_2$)—CH$_2$—COOH—aspartic acid
AspH HOOC—CH(NH$_2$)—CH$_2$—COO$^-$—aspartic acid anion Example 1. Comparative 118 g of amber acid and 25 g of calcium carbonate are dissolved in 600 ml of water at room temperature (~25° C.) (salt concentration—17.6% mass). The solution is poured over a paper filter and is incubated at room temperature for 24 hours. The solution is then slowly (for 20 min) heated to 100° C. and is evaporated at this temperature for 6 hours.

The resulting precipitated is dried to a constant mass. Yield (127.5 g)—100% of the theoretical.

Ca content (complexometric titration) corresponds to the ratio Ca:Suc=1:4; this is because the initial components are loaded in that same ratio, and all of the water is removed from the reaction mass. However, based on the NMR analysis (labeled carbon and hydrogen), the result is the mixture of complex calcium succinate salts, where about 84% is calcium tetrasuccinate and the remaining 16%—a mixture of less acidic calcium succinates (CaSuc, CaSuc$_2$, CaSuc$_3$) and complex calcium salts with the ratio Ca:Suc=1:5 and higher.

Example 2. Synthesis of Acidic Magnesium Succinate

3.7 L of water is loaded in the reactor and heated to 80-85° C. Amber acid (5.4 kg, 5% stoichiometric excess) is suspended in the water while stirring. At this temperature, 3.2-3.4 kg of amber acid in the form of a saturated aqueous solution of (concentration 41.2-44.5% mass) can be obtained.

After a 30-40 min incubation to stabilize the mixture, 925 g of magnesium oxide (95% purity) is added in portions with constant stirring. The stirring is continued at 80-85° C. until the solution of the complex salt is obtained—acidic magnesium succinate (concentration ~71% mass). After that the reaction mass is slowly (less than 0.5° C. per minute) cooled to ~75° C.—the temperature at which salt crystallization from the saturated solution begins, as well as dosage of the initial components.

Drying at 60-80° C. in a tray dryer allows obtaining dehydrated salts; drying under a warm air flow (30-40° C.) produces a tetrahydrate as the final product.

When drying with warm air (less then 50° C.), the resulting salt is tetra-aqueous crystal-hydrate with 98.8% mass of the main ingredient (complexometric titration). Magnesium content is 7.27% mass (atomic absorption spectrometry).

Example 3. Synthesis of Acidic Calcium Succinate

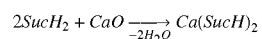

7.7 L of water is heated to 90-95° C. While stirring, 2.04 kg of amber acid (3% stoichiometric excess) is dissolved in the water and 577 g of calcium oxide (97% purity) is added slowly to the reaction zone, each portion is added after the previous one has dissolved. The resulting salt solution (with the concentration about 22% mass) is cooled to ~80° C., at which point crystallization of the precipitate begins. After that, the process is conducted as in example 2.

This allows to obtain both the dehydrated salt (drying at 105-110° C.) and the monohydrate (drying with warm air or vacuum at 30-40° C. and 15-20 mm Hg). The content of the main compound—acidic calcium succinate—at least 97%, content of the neutral salt (CaSuc.H$_2$O)—no more than 3% mass.

Example 4. Synthesis of Acidic Zinc Fumarate

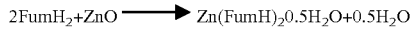

299.8 g of fumaric acid (1% stoichiometric excess) is dissolved in 9.62 L of water and heated to ~95° C. with stirring. 108 g of zinc oxide is slowly added to the solution (concentration about 3% mass) of fumaric acid, constantly stirring until the solution is formed. The solution is then cooled slowly (0.8-1.0° C.) until crystallization begins (~85° C.). After that, the synthesis of the salt is conducted at 80° C., forming precipitate is separated by filter; the concentrations of fumarate anion (or cation of zinc) are controlled by maintaining their constant amounts in the reaction volume (see Example 2).

After drying with vacuum (45-50° C., 15-20 mm Hg), salt $Zn(FumH)_2.0.5H_2O$ is obtained with 98.5% purity. Zn content—21.16% (X-ray fluorescence analysis).

Example 5. Synthesis of Acidic Magnesium Aspartate

$2AspH_2+MgO+3H_2O \longrightarrow Mg(AspH)_2.4H_2O$ 8.6 L of water is heated to 90-95° C. and 1.3 kg (~0.5% stoichiometric excess) of aspartic acid is added, stirred and a suspension (~750 g) of aspartic acid in its saturated solution (concentration ~6%) is obtained. 198.5 g of magnesium oxide (98.5% purity) is added in portions to the above solution with constant stirring. After mixing, a solution of magnesium aspartate (concentration ~17% mass) is obtained and is cooled until crystallization begins (65-70° C.). After that—see Example 2.

After drying (80° C., tray dryer) magnesium aspartate is obtained in the form of 4× water crystal-hydrate of 99.5% mass purity.

Example 6. Synthesis of Acidic Calcium Succinate Dihydrate

$2SucH_2+CaO+H_2O \longrightarrow Ca(SucH)_2.2H_2O$

640 L of water is loaded into a reactor and is heated to 70-75° C. 480 kg of 100% amber acid (from molar ratio AA:CaO=2.1:1) is added in portions while the reaction continues to heat to 80-85° C., until the acid is completely dissolved.

Water suspension of calcium hydroxide (which is obtained by slaking—108.5 kg of calcium oxide in 385 L of water in a working, preferably enameled container) is added in a small stream, slowly and evenly, while stirring.

The reaction mass is incubated in the reactor at 85-90° C., with stirring, for 1 day until the reaction is completed.

When the incubation is completed, the heat is turned off and, with a constant stirring, the reaction mass is cooled in two steps: first to ~70° C. (self-cooling), then to 16-18° C. by pouring cold water in the jacket of the reactor. Acidic calcium succinate crystallizes in the form of 2× water crystal-hydrate.

After crystallization is complete, the cooled suspension is filtered in several steps, in portions of about 150 L. All of the obtained wet precipitate is additionally separated from the solution by centrifugation until remaining water is ~5-7% mass. The precipitate is then dried.

The drying of the wet precipitate salt is conducted in the drying oven at 40-50° C.—to obtain acidic calcium succinate in the form of 2× water crystal-hydrate.

The total amount of dry product (acidic calcium succinate 2× hydrate) obtained from one round of synthesis is 485-506 kg.

Example 7. Zinc Fumarate, Acidic Monohydrate

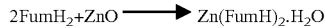

$2FumH_2+ZnO \longrightarrow Zn(FumH)_2.H_2O$

13 L of water is loaded in the reactor and, with constant heating and stirring, 11.9 kg of fumaric acid is suspended in it. The suspension is heated to ~60° C., and zinc oxide is added in portions (suspension prepared in a separate container immediately before this step, 4.17 kg of zinc oxide and 10 L of water). The reaction mass is then incubated for 2 hours with stirring (with partial evaporation), while continuously heated to 80-90° C.

After the incubation is completed, the heat is turned off and the cooling of the reaction mass to ~60° C. (self-cooling) is done with stirring. The reaction mass is then loaded into a crystallizer and cooled to 16-18° C.

The formed suspension is filtered in portions, the precipitate is wringed out and 18-20 kg of precipitate with ~30% moisture mass is obtained. The wet precipitate is dried in the warm air stream (40-50° C.). 14-15 kg of dry product is obtained; the main component makes up 99.2% (zinc content—20.86%).

Example 8. Testing the Incorporation of the Dicarboxylic Acid Anions (Components of the Produced Compounds) in Metabolic Processes For these studies, compounds were synthesized as described in examples 2-7, but using $^{13}C$-labeled amber, aspartic and fumaric acids. The signal incorporation in metabolism was determined by exhalation of the labeled $^{13}C$ atom in the form of $^{13}CO_2$. The experiment was conducted as follows: aqueous solutions, in the amounts equivalent to 1 mg of the acids anions they contained, were administered to rats (groups of 8 individuals, each rat weighing 225-250 g) with a pipette: amber acid, sodium fumarate (fumaric acid is almost insoluble in water), aspartic acids, $Ca(SucH)_2$, $Mg(SucH)2.4H_2O$, $Mg(AspH)_2.4H_2O$, $Zn(FumH)_2.0.5H_2O$, $Zn(FumH)_2.H_2O$. The animals were then quickly placed in a hermetically sealed chamber. The air from the chamber was sampled in the same amount as it was pumped in the chamber. The air collected 12 hours after solutions have been administered was analyzed for 13C content in $CO_2$; the baseline concentration was disregarded since it did not exceed 0.1%. After that, the mass % of 13C administer was calculated in the exhaled air. The following results were obtained: amber acid—99.4%, sodium fumarate—97.8%, aspartic acid—59.4%, $Ca(SucH)_2$—49.7%, $Mg(SucH)_2.4H_2O$—47.7%, $Mg(AspH)_2.4H_2O$—47.4%, $Zn(FumH)_2.0.5H_2O$—43.5%, $Zn(FumH)_2.H_2O$—41.4%. As the results clearly show, anions of all tested compounds are actively included in the cellular metabolic processes.

Having thus described a preferred embodiment, it should be apparent to those skilled in the art that certain advantages of the described method have been achieved.

It should also be appreciated that various modifications, adaptations, and alternative embodiments thereof may be made within the scope and spirit of the present invention. The invention is further defined by the following claims.

REFERENCES

1. Patent RU 2228183, published May 10, 2004.
2. Stephenson T. A. et al., "J. Chem. Soc", August 1964, 2538-2541.
3. Tomita Takeshi et al., "Bull. Chem. Soc. Japan", 1968, 41, No. 5, 1130-32.
4. Japanese patent No. 31606, cl. 30F34 (Ao/h), pub. 15.08.1972
5. *Referativnyi Zhurnal Khimiya* (Chemistry Journal Abstracts) (AJC), 1962, 28.11.1960, 20L280)

6. *Referativnyi Zhurnal Khimiya* (Chemistry Journal Abstracts) (AJC), 1963, 6.11.1961, $23H_{238}P$)
7. Japanese patent No. 24954 cl. 16B621, pr. 23.02. 1962, pub. 06.11.64
8. English patent No. 1129544
9. Japanese patent No. 13012
10. Japanese patent No. 49-8849
11. *J. Indian Chem. Soc.,* 1961, 38, No. 3, 153-4
12. Patent RU 02115657, pub. 20.07.1998

What is claimed is:

1. A method of obtaining a complex acidic salt of a divalent metal and a dicarboxylic acid, the method comprising:
   heating water in a reactor;
   adding a dicarboxylic acid to the heated water to produce a suspension of the dicarboxylic acid in the water;
   stirring the water to dissolve the dicarboxylic acid in the heated water so as to convert the suspension into a solution of the dicarboxylic acid in the heated water; during the stirring, and while the suspension is being converted to the solution, adding MeO to the reactor, where Me is a divalent metal, and
   wherein a molar ratio of the dicarboxylic acid and the MeO in the heated water is 2.005:1-2.1:1;
   continuing the stirring until formation of the complex acidic salt $Me(AcH)_2 \cdot nH_2O$ begins,
   where Ac is an anion of the dicarboxylic acid, and $0<=n<=8$;
   cooling the complex acidic salt to below a temperature of crystallization of the complex acidic salt;
   sedimenting the complex acidic salt;
   filtering the complex acidic salt to remove water from the complex acidic salt; and
   drying the complex acidic salt.

2. The method of claim 1, wherein the divalent metal is any of potassium, magnesium and zinc.

3. The method of claim 1, wherein the dicarboxylic acid is any of L-aspartic acid, L,D-aspartic acid, fumaric acid and amber acid.

* * * * *